United States Patent
Nabutovsky et al.

(10) Patent No.: US 7,200,437 B1
(45) Date of Patent: Apr. 3, 2007

(54) TISSUE CONTACT FOR SATELLITE CARDIAC PACEMAKER

(75) Inventors: Yelena Nabutovsky, Mountain View, CA (US); Sheldon Williams, Green Valley, CA (US); Mark W. Kroll, Simi Valley, CA (US); Buehl E. Truex, Glendora, CA (US); Rodney J. Hawkins, Saugus, CA (US); Adam Klonecke, Brentwood, CA (US); Anders Bjorling, Jarfalla (SE); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 267 days.

(21) Appl. No.: 10/964,910

(22) Filed: Oct. 13, 2004

(51) Int. Cl.
*A61N 1/365* (2006.01)

(52) U.S. Cl. .............................. 607/9; 607/36; 607/37; 607/129; 128/903

(58) Field of Classification Search ..................... 607/9, 607/33, 36–37, 129; 128/903
See application file for complete search history.

(56) References Cited

U.S. PATENT DOCUMENTS

| 4,030,509 | A | | 6/1977 | Heilman et al. ......... 128/419 D |
|---|---|---|---|---|
| 4,256,115 | A | | 3/1981 | Bilitch ................... 128/419 P |
| 5,300,110 | A | * | 4/1994 | Latterell et al. ............ 607/130 |
| 5,496,362 | A | | 3/1996 | KenKnight et al. ......... 607/129 |
| 5,814,089 | A | | 9/1998 | Stokes et al. .................. 607/32 |
| 5,916,243 | A | | 6/1999 | KenKnight et al. ......... 607/129 |
| 6,026,332 | A | | 2/2000 | Kenknight et al. ......... 607/129 |
| 6,032,079 | A | | 2/2000 | KenKnight et al. ......... 607/129 |
| 6,141,588 | A | | 10/2000 | Cox et al. ....................... 607/9 |
| 6,152,955 | A | | 11/2000 | KenKnight et al. ......... 607/129 |
| 6,360,129 | B1 | * | 3/2002 | Ley et al. .................... 607/127 |
| 6,718,212 | B2 | | 4/2004 | Parry et al. .................. 607/130 |
| 2005/0149157 | A1 | * | 7/2005 | Hunter et al. ................ 607/119 |

FOREIGN PATENT DOCUMENTS

| WO | WO 03/018110 A2 | 3/2003 |
|---|---|---|
| WO | WO 2003/018110 A3 | 3/2003 |

* cited by examiner

*Primary Examiner*—Robert Pezzuto
*Assistant Examiner*—Shevon Johnson

(57) ABSTRACT

An implantable cardiac system has a master pacing unit and a remote satellite pacing unit. The master pacing unit is electrically coupled to a right side of a patient's heart via a lead assembly. The satellite pacing unit is a leadless device mounted on the left side of the patient's heart and is wirelessly controlled by the master pacing unit. The satellite pacing unit is affixed to the heart by one or more mounting members. The base of the satellite unit case has a gel-like material which facilitates adhesion of the pacing unit to the heart tissue. The gel-like material promotes tissue growth to hold the pacing unit in place on the heart. The gel-like material may be composed of polyvinlpyrrolidone and may contain a steroid, such as dimethyl sulfoxide (DMSO), or dexamethazone sodium phosphate.

29 Claims, 7 Drawing Sheets

TISSUE CONTACT FOR SATELLITE CARDIAC PACEMAKER

FIELD OF THE INVENTION

The present invention generally relates to implantable cardiac devices for treating patients with heart conditions, such as congestive heart failure (CHF).

BACKGROUND

Biventricular pacing has proven to be an effective therapy for treating patients with congestive heart failure (CHF). CHF is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Unfortunately, when fitting a patient with an implantable pacing device, it can be difficult to pass a left-side lead into the coronary sinus vein, or the smaller final destination veins, or keep it in stable position. Accordingly, there is a need for alternative techniques of placing a pacing stimulus on the left side of the heart.

SUMMARY OF THE INVENTION

An implantable cardiac system has a master pacing unit and a remote satellite pacing unit. The master pacing unit is designed to be electrically coupled to one side (e.g., the right side) of a patient's heart via a lead assembly. The master pacing unit has a pulse generator to generate pacing pulses for application to the right ventricle and right atrium of the patient's heart and a communications module to transmit pacing commands to the satellite pacing unit via a wireless link.

The satellite pacing unit may be a leadless device designed to be mounted on the other (e.g., left) side of the patient's heart. The satellite pacing unit can be implanted, for example, using prophylactic techniques during bypass surgery or using a thoracoscopic procedure during implant of the master pacing unit. The satellite pacing unit comprises a housing and an elongated, advantageously helical, member with which the satellite pacing unit may be attached to the heart. Additionally, the satellite pacing unit has a gel-like material on its base which facilitates, among other features, adherence of the satellite pacing unit to the heart. The gel-like material may be composed of polyvinlpyrrolidone and may contain a steroid, such as dimethyl sulfoxide (DMSO), or dexamethazone sodium phosphate.

In a further embodiment, the satellite pacing unit includes projections on its base. These projections aid in retaining the satellite pacing unit in place against the wall of the heart.

The satellite pacing unit has a communications module to receive the pacing commands from the master pacing unit and a pulse generator to generate pacing pulses for application to the left ventricle of the patient's heart. In one mode of operation, the satellite pacing unit applies left ventricle pacing pulses in response to the pacing commands received from the master pacing unit. In this manner, the system supports multi-chamber pacing, whereby pulses are applied to the right chambers via the lead assembly and to the left chambers via the remotely controlled, leadless satellite pacing unit.

DETAILED DESCRIPTION OF THE INVENTION

Overview

In the following discussion, an implantable cardiac system is described that treats patients with congestive heart failure (CHF). The implantable cardiac system has a master pacing unit that applies pacing pulses to the right side of the heart via a lead assembly, and a remote leadless satellite pacing unit that applies pacing pulses to the left side of the heart under the direction of the master pacing unit.

Implantable Cardiac System

Figure 1:
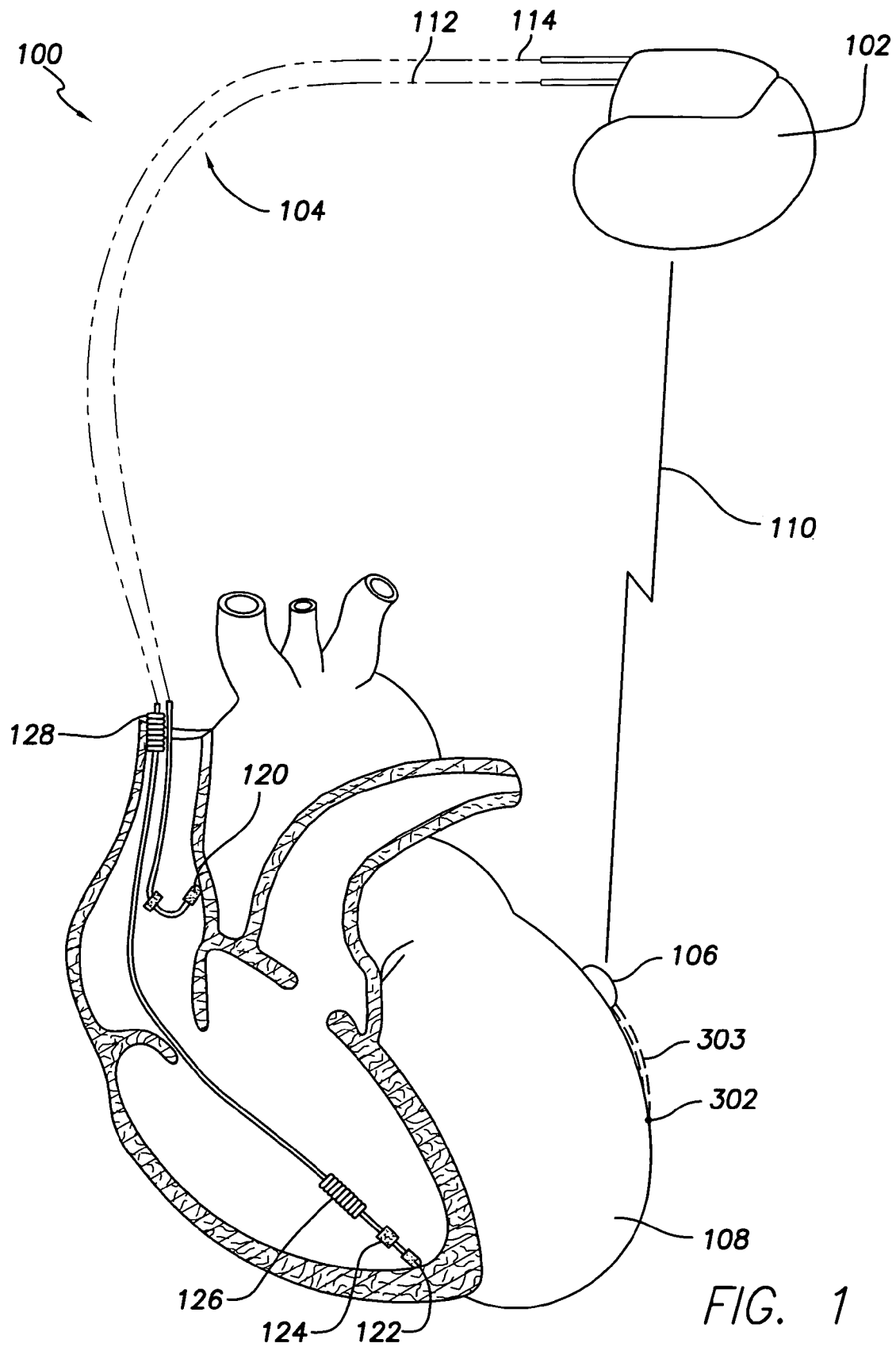
FIG. 1 is a diagrammatic illustration of an implantable cardiac system mounted in electrical communication with a patient's heart for sensing and multi-chamber stimulation therapy.

FIG. 1 shows an exemplary implantable cardiac system 100 having a master pacing unit 102, a lead assembly 104, and a remote leadless satellite pacing unit 106. The implantable cardiac system 100 supports multi-chamber detection and stimulation therapy, including biventricular pacing to treat a patient with CHF. The lead assembly 104 interconnects the master pacing unit 102 with the right side of the patient's heart 108. The satellite pacing unit 106 is mounted on the left side of the heart, and particularly to the left ventricle. The satellite pacing unit 106 can be mounted, for example, using prophylactic techniques during bypass surgery or using a thoracoscopic procedure during implant of the master pacing unit 102. The satellite pacing unit 106 communicates with the master pacing unit 102 using wireless communication technologies, such as high frequency modulation, as represented by link 110.

In the illustrated implementation, the lead assembly 104 has two right-sided leads: a right atrial lead 112 and a right ventricular lead 114. The right atrial lead 112 supports an atrial tip electrode 120, which is implanted in the patient's right atrial appendage. The right atrial lead 112 enables the master pacing unit 102 to sense atrial cardiac signals and apply pacing therapy to the right atrial chamber.

The right ventricular lead 114 is electrically coupled to a right ventricular tip electrode 122, a right ventricular ring electrode 124, a right ventricular (RV) coil electrode 126, and an SVC (superior vena cava) coil electrode 128. The right ventricular lead 114 is transvenously inserted into the heart 108 to place the right ventricular tip electrode 122 in the right ventricular apex so that the RV coil electrode 126 will be positioned in the right ventricle and the SVC coil electrode 128 will be positioned in the superior vena cava. Accordingly, the right ventricular lead 114 is capable of receiving cardiac signals, and delivering stimulation in the form of pacing and shock therapy to the right ventricle. It is noted that the RV coil electrode 126 is optional, and may not be present in certain low voltage implementations. While the satellite unit cannot deliver high voltage (HV) shock therapy, it can contribute to HV shock therapy by enabling better detection of arrhythmias. By noting an irregularity between the EGM seen by the satellite unit and the RV lead, one can detect fibrillation with confidence.

The leadless satellite pacing unit 106 is positioned on the left ventricle of the heart 108. It is capable of administering left chamber pacing therapy under the direction of the master pacing unit 102. The satellite pacing unit 106 may also be equipped with sensing circuitry to sense artifacts generated by the master pacing unit during right side pacing. In one implementation, the satellite pacing unit 106 applies pacing pulses in response to commands communicated from the master pacing unit 102. In another implementation, the satellite pacing unit 106 senses the master artifacts and applies pacing pulses in response. In yet another implementation, the satellite pacing unit 106 applies pacing pulses in response to a combination of sensed master artifacts and commands from the master pacing unit.

Although not illustrated, the implantable cardiac system 100 may be configured to support more than one remote satellite pacing unit. A physician may elect to mount multiple satellite pacing units 106 at different positions of the heart. The physician is then able to evaluate various satellite pacing units 106 to determine which one is most effective at applying the pacing pulses. In another technique, the physician might elect to implant multiple satellite pacing units in physical proximity, initially turning all units off. Then, after implantation, the physician can activate the satellite pacing units one at a time, as needed, as units run low on batteries or experience problems that preclude effective operation (e.g., electrode dislodges).

As another alternate configuration, the system 100 can be configured to support triple timing optimal ventricular pacing to obtain optimal hemodynamics. For example, one satellite unit is placed 1 cm down from the ventricular base by the lateral cardiac vein while a second satellite is placed 3 cm down by the same vein. Then, the first satellite unit is paced and the second is paced 10 ms later, and finally, the RV tip electrode is paced another 15 ms later. Similarly, this is extendable to four or more left sided satellite units.

Figure 2:
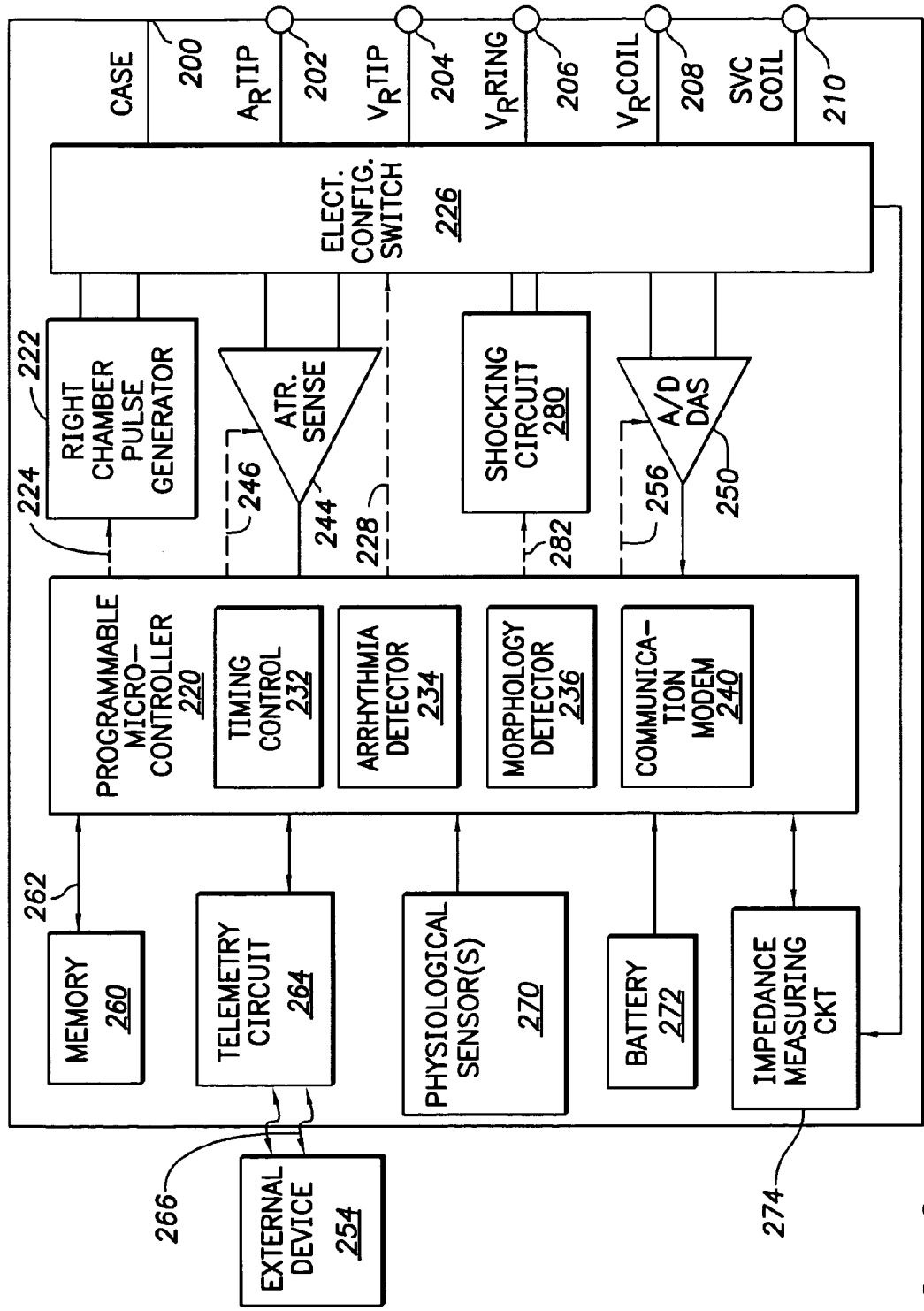
FIG. 2 is a block diagram of a master pacing unit employed in the implantable cardiac system.

It is further noted that the remote pacing units can be put in hibernation upon transmission of a deactivation signal from the master pacing unit, or on command of an external programmer (not shown in FIG. 1, but illustrated in FIG. 2).

Exemplary Master Pacing Unit

FIG. 2 shows an exemplary master pacing unit 102 that is implanted into the patient as part of the implantable cardiac system 100. The master pacing unit 102 may be implemented as a full-function biventricular pacemaker, equipped with both atrial and ventricular sensing and pacing circuitry for four chamber sensing and stimulation therapy (including both pacing and shock treatment). Alternatively, the master pacing unit 102 may be implemented with a reduced set of functions and components. For instance, the master pacing unit may be implemented without ventricular sensing and pacing because such functions can be implemented at the remote satellite pacing unit 106. For discussion purposes, this latter reduced-function implementation will be described.

The master pacing unit 102 has a housing 200 to hold the electronic/computing components. The housing 200 (which is often referred to as the "can", "case", "encasing", or "case electrode") may be programmably selected to act as the return electrode for certain pacing modes. Housing 200 further includes a connector (not shown) with a plurality of terminals 202, 204, 206, 208, and 210. The terminals are shown schematically and, for convenience, the names of the electrodes to which they are connected are identified. The terminals include:

- a right atrial tip terminal (AR TIP) 202 for atrial tip electrode 120;
- a right ventricular tip terminal (VR TIP) 204 for right ventricular tip electrode 122;
- a right ventricular ring terminal (VR RING) 206 for right ventricular ring electrode 124;
- a right ventricular shocking terminal (VR COIL) 208 for right ventricular coil electrode 126; and
- an SVC shocking terminal (SVC COIL) 210 for SVC coil electrode 128.

The master pacing unit 102 includes a programmable microcontroller 220 that controls various operations of the master pacing unit 102, including cardiac monitoring and stimulation therapy. Microcontroller 220 includes a microprocessor (or equivalent control circuitry), RAM and/or ROM memory, logic and timing circuitry, state machine circuitry, and I/O circuitry.

Master pacing unit 102 further includes a right chamber pulse generator 222 that generates pacing stimulation pulses for delivery by the right atrial lead 112 and/or the right ventricular lead 114 to the right chambers of the heart. The pulse generator 222 is controlled by the microcontroller 220 via control signal 224. The right chamber pulse generator 222 is coupled to the lead assembly 104 via an electrode configuration switch 226, which includes multiple switches for connecting the desired electrodes to the appropriate I/O circuits, thereby facilitating electrode programmability. The switch 226 is controlled by a control signal 228 from the microcontroller 220.

Microcontroller 220 is illustrated as including timing control circuitry 232 to control the timing of the stimulation pulses (e.g., pacing rate, atrio-ventricular (AV) delay, atrial interconduction (A—A) delay, or ventricular interconduction (V—V) delay, etc.). The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector 236. Although not shown, the microcontroller 220 may further include other dedicated circuitry and/or firmware/software components that assist in monitoring various conditions of the patient's heart and managing pacing therapies.

The master pacing unit 102 is further equipped with a communication modem (modulator/demodulator) 240 to enable wireless communication with the remote satellite pacing unit 106. In one implementation, the communication modem 240 uses high frequency modulation. As one example, the modem 240 transmits signals between a pair of electrodes of the lead assembly 104, such as between the can 200 and the right ventricular tip electrode 122. The signals are transmitted in a high frequency range of approximately 20–80 kHz, as such signals travel through the body tissue in fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The master pacing unit 102 has right chamber sensing circuitry 244 selectively coupled to the right atrial lead 112 and the right ventricular lead 114 through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and a threshold detection circuit to selectively sense the cardiac signal of interest. The automatic gain control enables the unit 102 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the right chamber sensing circuitry 244 is connected to the microcontroller 220 which, in turn, triggers or inhibits the right chamber pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

The master pacing unit 102 further includes an analog-to-digital (A/D) data acquisition system (DAS) 250 coupled to the lead assembly 104 via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the master pacing unit 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 108 within each respective tier of therapy.

The operating parameters of the master pacing unit 102 may be non-invasively programmed into the memory 260 through a telemetry circuit 264 in telemetric communication via communication link 266 with the external device 254. The telemetry circuit 264 allows intracardiac electrograms and status information relating to the operation of the master pacing unit 102 (as contained in the microcontroller 220 or memory 260) to be sent to the external device 254 through the established communication link 266.

The master pacing unit 102 can further include magnet detection circuitry (not shown), coupled to the microcontroller 220, to detect when a magnet is placed over the unit. A magnet may be used by a clinician to perform various test functions of the unit 102 and/or to signal the microcontroller 220 that the external programmer 254 is in place to receive or transmit data to the microcontroller 220 through the telemetry circuits 264.

The master pacing unit 102 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V—V Delay, etc.) at which the atrial and ventricular pacing pulses are administered. While shown as being included within the unit 102, the physiologic sensor(s) 270 may be external to the unit 102, yet still be implanted within or carried by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the master pacing unit 102. The battery 272 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 102 employs lithium/silver vanadium oxide batteries.

The master pacing unit 102 further includes an impedance measuring circuit 274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The master pacing unit 102 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5–10 joules), or high energy (e.g., 11 to 40 joules), as controlled by the microcontroller 220. Such shocking pulses are applied to the patient's heart 108 through shocking electrodes selected, for example, from the right atrial coil electrode 126 and the SVC coil electrode 128.

The master pacing unit 102 can be programmed to treat CHF by applying pacing to the right atrial and right ventricle via leads 112 and 114 and communicating with the remote satellite pacing unit 106 to pace the left ventricle. One or more satellite pacing units can be operated under the control of the master pacing unit 102. Different implementations of the satellite pacing units are described next.

Exemplary Satellite Pacing Units

The satellite pacing unit 106 is implanted into the patient as part of the implantable cardiac system 100 and preferably mounted on or proximal to the left ventricle. The satellite pacing unit 106 may be implemented in many ways, depending upon the functionality desired in the remote unit. The unit may be configured as complex as a full-function pacemaker with multi-chamber sensing and pulse generation capabilities, or more simply with a reduced set of functionality. Three exemplary implementations are described.

Passive Satellite

Figure 3:
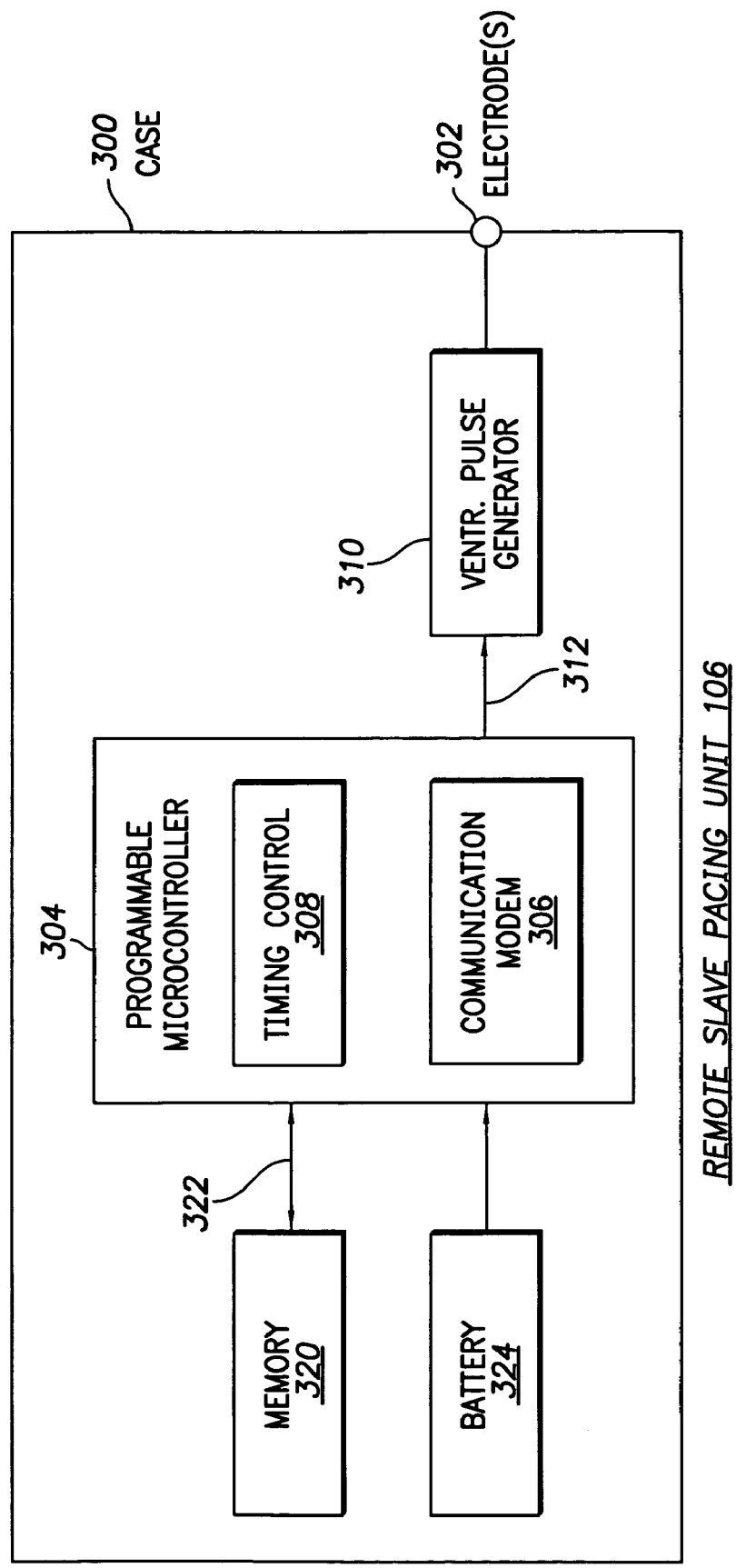
FIG. 3 is a block diagram of a first implementation of a satellite pacing unit employed in the implantable cardiac system.

FIG. 3 shows one exemplary satellite pacing unit 106 that has minimal functionality. In this example, the satellite pacing unit 106 is configured as a simple passive device that paces the left ventricle in response to commands from the master pacing unit 102. The satellite pacing unit 106 has a housing 300 to hold and protect the electronic/computing components. One or more electrodes 302 are mounted in the housing 300 to deliver pacing pulses to the heart tissue. The electrode(s) and/or a separate anchor mechanism can be used to secure the satellite pacing unit 106 to the left ventricle, as shown in FIG. 1. In an alternate embodiment, one or more of the electrodes 302 are mounted on one or more leads 303 (shown in phantom in FIG. 1) extending from the housing 300, which allows the one or more electrodes to be spaced from the housing 300. For example, one or more electrodes 302 could be mounted on the housing 300 for placement at a first location (e.g., adjacent to the left atrium), and another electrode or electrodes 302 could be connected to lead 303 for placement at a second location (e.g., adjacent to the left ventricle).

The satellite pacing unit 106 includes a programmable microcontroller 304 to control the pacing operation of the satellite pacing unit. A communication modem 306 is provided to facilitate wireless communication with the master pacing unit 106 using high frequency modulation. The communication modem 306 may be implemented in hardware as part of the microcontroller 304, or as software/firmware instructions programmed into and executed by the microcontroller 304. Alternatively, the modem may reside separately from the microcontroller as a standalone component. Microcontroller 304 may be further equipped with timing control circuitry 308 to control the timing of the stimulation pulses being applied to the left ventricle in response to command signals received via communication modem 306 from the master pacing unit 102.

The satellite pacing unit 106 has a ventricular pulse generator 310 to generate pacing stimulation pulses for delivery by the electrode 302. The ventricular pulse generator 310 is controlled by the microcontroller 304 via control signal 312.

The microcontroller 304 is coupled to a memory 320 via data/address bus 322. Any programmable operating parameters to be used by the microcontroller 304 can be stored in memory 320 and used to customize the operation of the satellite pacing unit 106 to suit the needs of a particular patient. Such operating parameters can be programmed into the memory 320 via instructions transmitted from the master pacing unit to the satellite pacing unit 106, where they are received at the communication modem 306 and stored in the memory 320. In simpler constructions, where no programmable operating parameters are employed or desired, the memory 320 and bus 322 may be omitted.

The satellite pacing unit 106 further includes a battery 324 to supply operating power to all of the components shown in FIG. 3. The battery 324 is capable of operating at low current drains for long periods of time (e.g., less than 10 μA), and is capable of providing pulses of sufficient voltage and current to apply pacing to the heart. As one example, the battery 324 is implemented as one or more lithium/silver vanadium oxide batteries.

In the FIG. 3 configuration, the satellite pacing unit 106 delivers a pacing pulse to the patient's left ventricle in response to commands transmitted from the master pacing unit 102. The commands are communicated via the wireless link 110 to the communication modem 306. The commands are processed by the microcontroller 304. Once received and processed, the satellite pacing unit 106 passively responds by generating a pacing pulse at the pulse generator 310 and delivering the pulse via the electrode(s) 302. The pulse may be applied immediately, or after some timing delayed dictated by the timing control circuitry 308.

Passive Satellite with Sensing Capabilities

Figure 4:
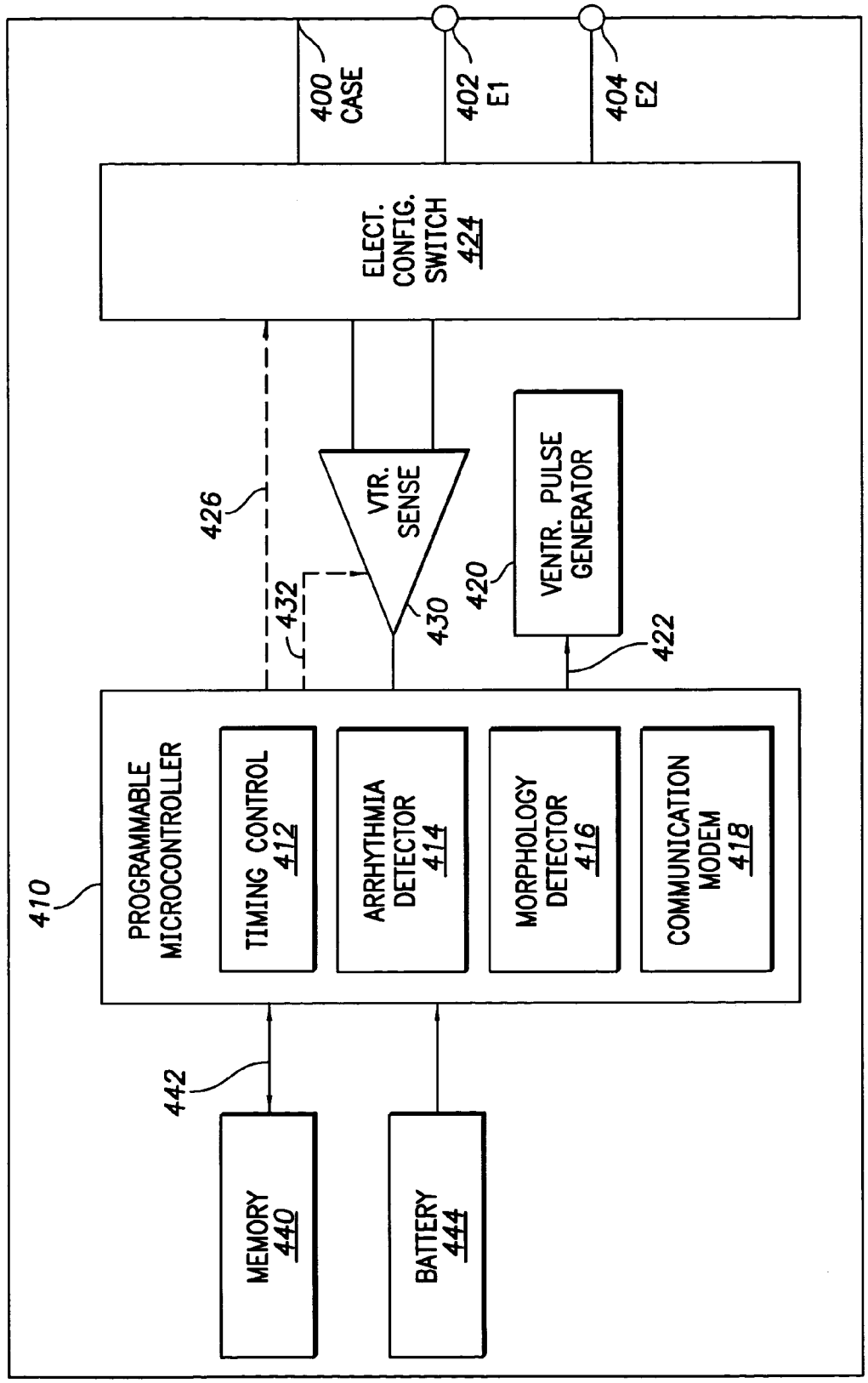
FIG. 4 is a block diagram of a second implementation of a satellite pacing unit employed in the implantable cardiac system.

FIG. 4 shows another exemplary satellite pacing unit 106', which is implemented with more functionality than that of the satellite pacing unit 106 of FIG. 3. In this example, the satellite pacing unit 106' is configured with sensing capabilities and diagnostic detection capabilities that is more akin to a full-function pacemaker. The satellite pacing unit 106' has a housing 400 to hold and protect the electronic/computing components. Housing 400 has a connector (not shown) with a plurality of terminals for connections to associated electrodes. The terminals include a first electrode (E1) 402 and a second electrode (E2) 404. More or less electrodes may be used in other configurations. Since the combination of the central electrode and the housing serve as a sensing dipole, no additional electrodes are needed for sensing and pacing. So, the satellite pacing unit 106' could function as a WI pacemaker. However, with additional electrodes the satellite pacing unit 106' could detect other signals (such as far-field P-waves) to allow more sophisticated modes of operation.

The satellite pacing unit 106' includes a programmable microcontroller 410 that controls various operations of the pacing unit, including cardiac monitoring and stimulation therapy. Timing control circuitry 412 may be configured to control the timing of the stimulation pulses applied via the electrodes 402 and 404. Together with the timing stipulated by the master pacing unit for the right atrium and right ventricle, the timing control circuitry 412 may be used to time stimulation pulses (e.g., pacing rate, atrio-ventricular (AV) delay, atrial interconduction (A—A) delay, or ventricular interconduction (V—V) delay, etc.), refractory periods, blanking intervals, noise detection windows, evoked response windows, alert intervals, marker channel timing, and so on.

Microcontroller 410 has an arrhythmia detector 414 for detecting arrhythmia conditions and a morphology detector 416 for detecting morphological-related parameters. The satellite pacing unit 106' is further equipped with a communication modem 418 to facilitate wireless communication with master pacing unit 102 using high frequency modulation.

The satellite pacing unit 106' further includes a ventricular pulse generator 420 to generate pacing stimulation pulses for delivery by the electrodes 402 and 404 to the left ventricle of the patient's heart. The ventricular pulse generator 420 is controlled by the microcontroller 420 via control signal 422 and is coupled to the leads 400–404 via an electrode configuration switch 424. The switch 424 includes one or more switches for connecting the desired electrodes to the appropriate I/O circuits, thereby providing electrode programmability. The microcontroller 410 controls the switch 424 via a control signal 426.

In the illustrated implementation, the satellite pacing unit 106' is equipped with ventricular (VTR. SENSE) sensing circuit 430, which can be selectively coupled to electrodes 402 and 404 to detect the presence of cardiac activity in the left ventricle of the heart. The ventricular sensing circuit 430 may include dedicated sense amplifiers, multiplexed amplifiers, or shared amplifiers. It may employ one or more low power, precision amplifiers with programmable gain and/or automatic gain control, bandpass filtering, and a threshold detection circuit, to selectively sense the cardiac signal of interest. The ventricular sensing circuit 430 is controlled by the microcontroller 410 via control signal 432.

The microcontroller 410 is coupled to a memory 440 via data/address bus 442 to store various programmable operating parameters used to customize operation of the satellite pacing unit 106'. Operating parameters can be programmed into the memory 440 via instructions transmitted from the master pacing unit to the satellite pacing unit 106', where they are received at the communication modem 418 and stored in the memory 440. The unit 106' further has a battery 444 to provide power to all components in the unit. The battery 444 also provides power for the stimulation pulses.

In the FIG. 4 configuration, the satellite pacing unit 106' can deliver pacing pulses to the patient's left ventricle in response to commands transmitted from the master pacing unit 102. This is similar to the satellite pacing unit 106 of FIG. 3. Such commands are communicated via the wireless link 110 to the communication modem 418. Once received, the satellite pacing unit 106' responds by generating a pacing pulse at the pulse generator 420 and delivering the pulse via the electrode(s) 402 and 404.

Additionally, the satellite pacing unit 106' can be configured to deliver pacing pulses in response to detection of a pacing artifact induced by the master pacing unit. The master pacing unit 102 delivers a pacing pulse to the right side of the patient's heart to initiate a contraction. The ventricular sensing circuit 430 resident at the satellite pacing unit 106' detects the pacing spike and delivers its own properly timed pacing pulse to the left ventricle. The pacing pulse could be applied instantaneously upon detection of the master pacing pulse, or after some programmed delay. The advantage of the artifact sensing mode of operation is that the programming and communication schemes are easier to implement. A disadvantage of the sensing mode, however, is that the satellite pacing unit 106' is unable to pulse before the master pacing unit 102. This disadvantage can be overcome, however, by operating the unit in both the artifact sensing mode and the command-responsive mode, whereby the master pacing unit can send a pacing command directing the satellite pacing unit to pace before delivery of the master pacing pulse.

Active Satellite

Figure 5:
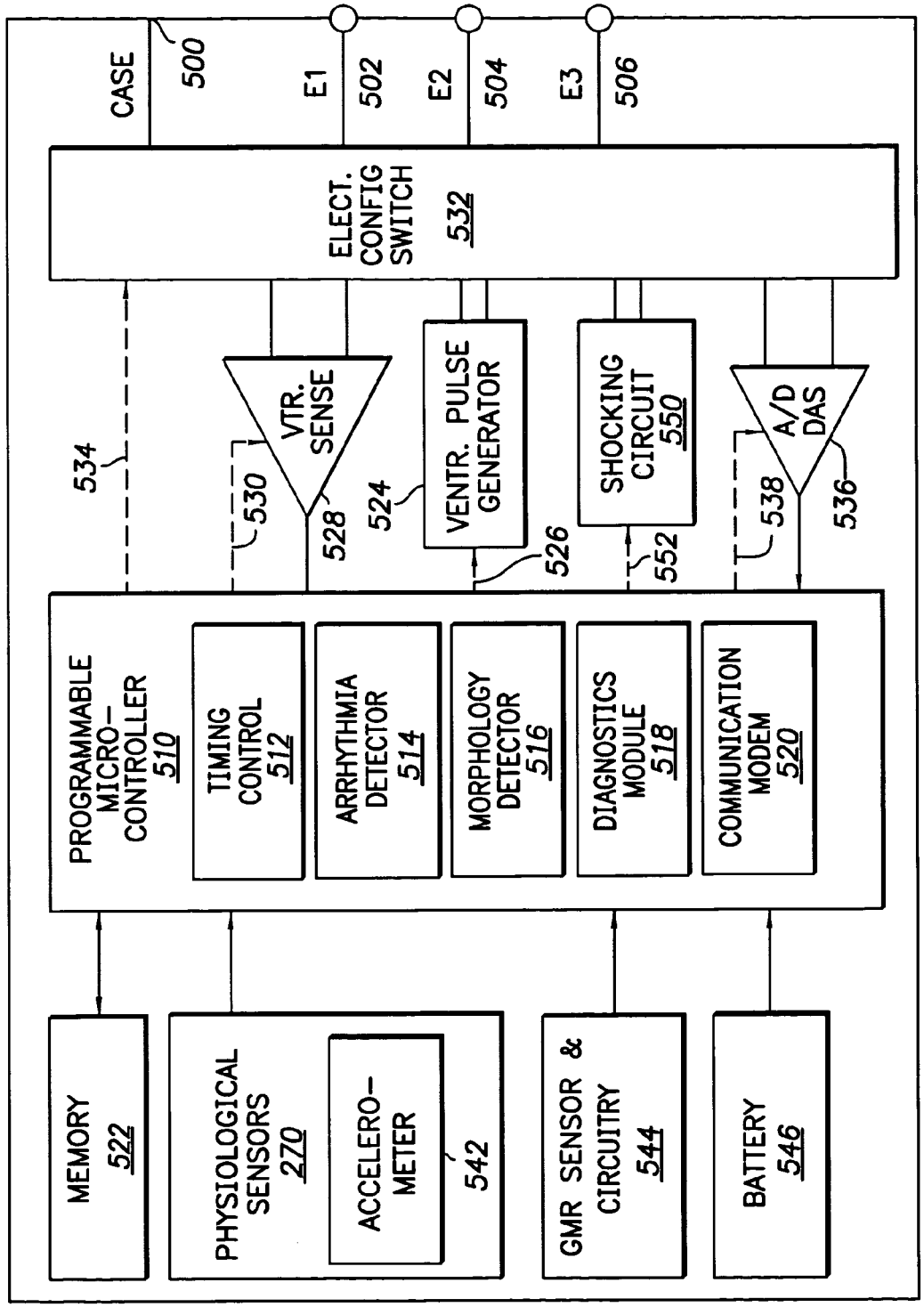
FIG. 5 is a block diagram of a third implementation of a satellite pacing unit employed in the implantable cardiac system.

FIG. 5 shows another exemplary satellite pacing unit 106" configured as a full-function device capable of sensing, pacing, and diagnostic feedback, as well as two-way communication. The unit 106" includes a housing 500 that supports electrode (E1) 502, electrode (E2) 504, and electrode (E3) 506. The unit may be configured to support more or less electrodes in other configurations. The electrodes allow the satellite pacing unit 106" to achieve left chamber sensing and pacing. Representative electrodes include a left ventricular tip electrode, and two widely separated point electrodes to sense the far-field atrial signals.

A programmable microcontroller 510 controls various modes of stimulation therapy. It also collects diagnostic information and returns the information to the master pacing unit 102, which may then communicate the information to an external device 254 (see FIG. 2) for review by the physician. The microcontroller 510 includes a microprocessor, or equivalent control circuitry, designed specifically for controlling the delivery of stimulation therapy, and may further include RAM or ROM memory, logic and timing circuitry, state machine circuitry, and I/O circuitry.

Microcontroller 510 includes timing control circuitry 512, an arrhythmia detector 514, a morphology detector 516, a diagnostics module 518, and a communication modem 520. The diagnostics module 518 collects data sensed by the satellite pacing unit 106". A memory 522 is coupled to the microcontroller 510 to store the data captured by the satellite pacing unit, as well as any operating parameters used by the microcontroller 510.

The communication modem 520 offers both reception and transmission capabilities. In this manner, the communication modem 520 receives command instructions from the master pacing unit 102 via wireless link 110 and uses the instructions for pacing or shock therapies, as well as to alter programming parameters of the microcontroller 510. Additionally, the communication modem 520 can be used to transmit data collected by the satellite pacing unit 106" back to the master pacing unit 102 via the wireless link 110. The data may be used by the master pacing unit 102 to identify various conditions and to administer therapies in response. Thus, data collected by the satellite pacing unit 106" may be stored locally in memory 522, at the master pacing unit 102, and/or transmitted out to the external device 254 (FIG. 2).

The satellite pacing unit 106" has a ventricular pulse generator 524 to generate pacing stimulation pulses for delivery by one or more electrodes 502–506. The microcontroller 510 controls the ventricular pulse generator 524 via a control signal 526. Ventricular sensing circuit 528 is employed to sense the presence of cardiac activity in one or both of the left chambers of the heart. The sensing circuit 528 receives a control signal 530 from the microcontroller 510 for purposes of controlling the gain, threshold, polarization charge removal circuitry, and the timing of any blocking circuitry.

An electronic configuration switch 532 connects the pulse generator 524 and sensing circuit 528 to the desired electrodes. In response to a control signal 534 from the microcontroller 510, the switch 532 makes the proper connections to the electrodes.

The satellite pacing unit 106" utilizes the ventricular sensing circuit 528 to sense cardiac activity, including inherent beats and pacing artifacts. Sensed cardiac activity can be used by the arrhythmia detector 514 to classify arrhythmias. Sensed artifacts may be used to trigger pacing in the satellite pacing unit, as is described below in more detail.

An analog-to-digital (A/D) data acquisition system (DAS) 536 acquires intracardiac electrogram signals, converts the raw analog data into a digital signal, and stores the digital signals for later processing and/or transmission to the master pacing unit 102. The data acquisition system 536 is coupled to the various electrodes through the switch 532 to sample cardiac signals across desired electrodes. The microcontroller 510 controls operation of the data acquisition system 536 via control signal 538.

The data acquisition system 536 may be used to detect an evoked response from the heart in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 510 detects a depolarization signal during a window following a stimulation pulse, the presence of which indicates that capture has occurred. The microcontroller 220 enables capture detection by triggering the ventricular pulse generator 524 to generate a stimulation pulse, starting a capture detection window using the timing control circuitry 512 within the microcontroller 510, and enabling the data acquisition system 536 via control signal 538 to sample the cardiac signal that falls in the capture detection window and, based on the amplitude, determines if capture has occurred.

The satellite pacing unit 106" can further include one or more physiological sensors 540 which may be used to detect changes in cardiac output, changes in the physiological condition of the heart, or diurnal changes in activity (i.e., detecting sleep and wake states). While shown as being included within the unit housing, the physiologic sensors 540 may be external to the housing, yet still be implanted within or carried by the patient. Examples of physiologic sensors include sensors that sense respiration rate, pH of blood, ventricular gradient, and so forth. Another sensor that may be used is one that detects activity variance, wherein an activity sensor is monitored diurnally to detect the low variance in the measurement corresponding to the sleep state.

One specific type of physiological sensor is a three-dimensional (3D) accelerometer-based sensor 542 that measures the acceleration resulting from the patient's movement. The accelerometer can be used to sense a contraction and/or body movement. The signals are passed to the microcontroller 510 for analysis in determining whether the sensed acceleration pertains to a contraction or indicates that the patient is undergoing heightened physical exertion or is moving directionally upwards (e.g., walking upstairs) or downwards (e.g., reclining for sleep or rest). The microcontroller 510 may use the information to adjust the pacing rate or invoke various pacing therapies.

The satellite pacing unit 106" may also be equipped with a GMR (giant magneto resistance) sensor and circuitry 544 that detects the earth's magnetic fields. The GMR sensor and circuitry 544 may be used to ascertain absolute orientation coordinates based on the earth's magnetic fields. The device is thus able to discern a true vertical direction regardless of the patient's position (i.e., whether the patient is lying down or standing up). The three-axis orientation coordinates measured by the 3D accelerometer-based sensor 542 may then be taken relative to the absolute orientation coordinates from the GMR. For instance, as a person sits up, the axial coordinates of the 3D accelerometer-based sensor 544 might change by 90°, but the sensor signals may be calibrated as to the true vertical direction based on the output of the GMR sensor and circuitry 544.

A battery 546 provides operating power to all of the circuits, as well as for the pacing and shocking pulses. For shocking therapy, the battery 546 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 546 has a predictable discharge characteristic so that elective replacement time can be detected.

In the case where the remote unit 106" is intended to operate as an implantable cardioverter/defibrillator (ICD) device, the microcontroller 510 detects the occurrence of an arrhythmia and automatically applies an appropriate electrical shock therapy to the heart aimed at terminating the detected arrhythmia. The microcontroller controls a shocking circuit 550 by way of a control signal 552 to generate shocking pulses of low (up to 0.5 joules), moderate (0.5–10 joules), or high energy (11 to 40 joules). The shocking can be applied solely by the remote satellite pacing unit 106" or in concert with the master pacing unit 102.

In the FIG. 5 configuration, the satellite pacing unit 106" offers a full range of functionality. It can deliver pacing pulses to the patient's left ventricle in response to commands transmitted from the master pacing unit 102. It is also capable of detecting a pacing artifact induced by the master pacing unit and delivering a responsive pacing pulse. Additionally, the remote satellite pacing unit can be programmed to a failsafe mode that requires it to (1) sense either an inherent R wave or a pacing spike administered by the master pacing unit, in addition to (2) receiving a pacing command from the master pacing unit. Furthermore, with two-way communication, the satellite pacing unit is able to provide diagnostic information to the master pacing unit. The two units could also be configured to cooperate for ventricular fibrillation (VF) detection by noting cross-chamber de-correlation.

Attachment of Satellite Pacing Unit to Heart Tissue

FIGS. 6–9 relate to the construction of the casing or "can" of the leadless satellite pacing unit 106 and the manner in which the satellite pacing unit is attached to the heart tissue. As noted above, the leadless satellite pacing unit 106 is typically positioned on the left ventricle of the heart.

Figure 6:
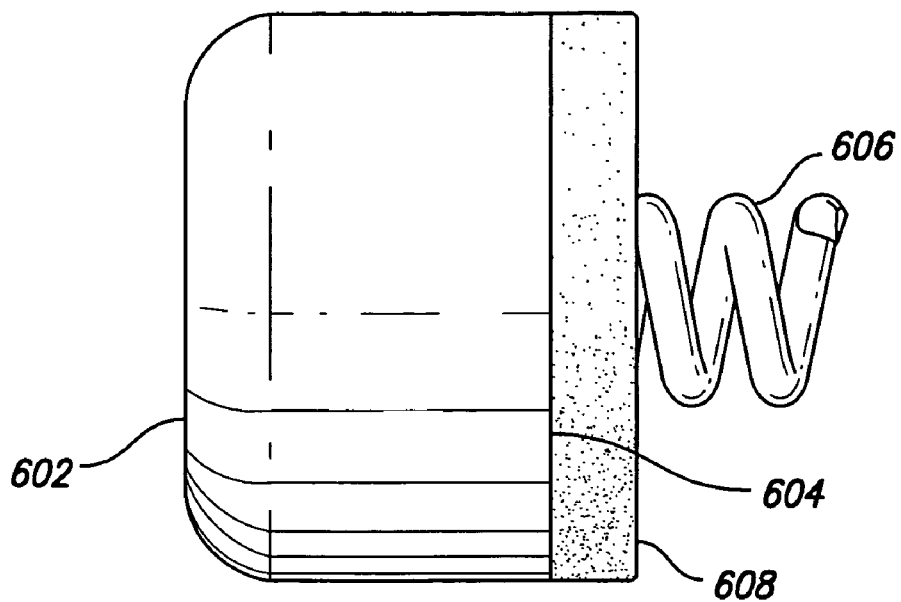
FIG. 6 is a side view of one embodiment of a satellite pacing unit.
Figure 7:
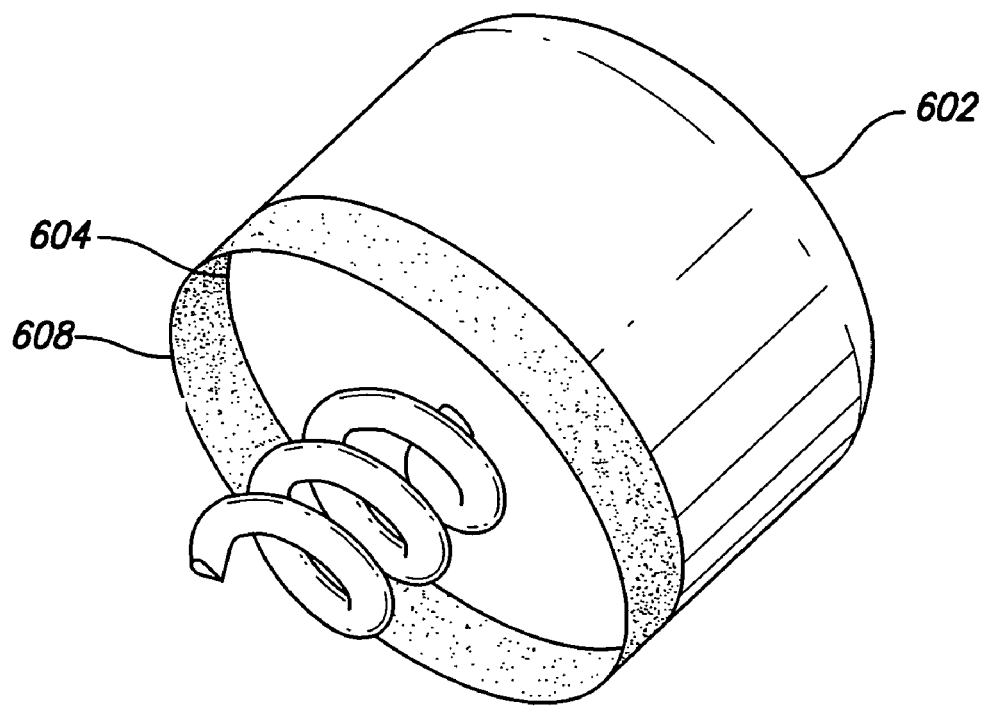
FIG. 7 is a perspective view of the satellite pacing unit shown in FIG. 6.

FIGS. 6–7 show one embodiment of satellite pacing unit 106. Unit 106 has a housing or casing 602 in which all of the operating components for the satellite pacing unit described above are contained. Casing 602 has a base portion 604. An elongated member 606 extends out of casing 602 through base 604. Advantageously, member 606 has a helical or screw-like shape. This permits member 606 to penetrate the pericardium and to be "screwed" into the epicardium of the heart.

A soft gel-like material 608 is affixed to base portion 604 of casing 602. Gel-like material 608 may be affixed to base portion 604 by any well known medical adhesive. Gel-like material 608 facilitates attachment of pacing unit 106 to the heart tissue and to absorb shocks as the heart beats and moves. Material 608 promotes tissue growth and allows tissue to grow into material 608 to hold device 106 in place on the heart. Gel-like material 608 may be composed of polyvinlpyrrolidone and may contain a steroid, such as dimethyl sulfoxide (DMSO), or dexamethazone sodium phosphate. The steroid is eluted to reduce the immune response of the body and to aid in preventing irritation and inflammation of the tissue affected by affixing the casing 602 thereto and further aids the healing process following implantation of unit 106. The steroid could be incorporated into the gel as a powder to be released under appropriate temperature conditions or when it comes into contact with blood.

Gel-like material 608 is conductive, as are elongated members 606 and casing 602. This defines an electrical circuit path to enable satellite pacing unit 106 to transmit pacing pulses to the heart.

Member 606 may also be made to elute a steroid. Specifically, member 606 may have a pellet or rod containing a steroid eluding solution within the helix of the screw.

Alternatively, member 606 may be coated with a steroid eluting solution, such as Napthion. Once member 606 is screwed into the epicardium, the steroid interacts with the epicardium to reduce irritation and promote healing of the affected tissue region.

Figure 8:
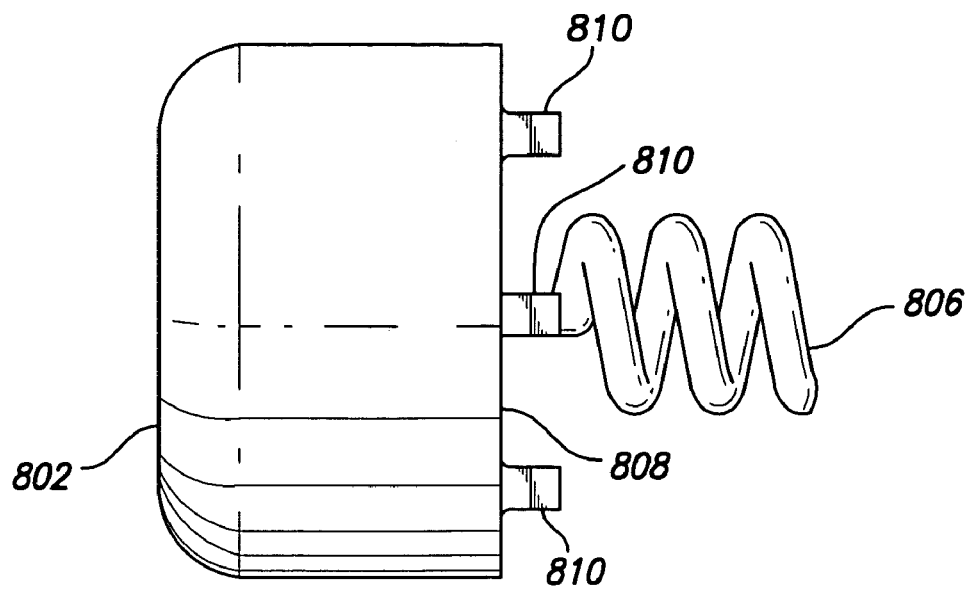
FIG. 8 is a side view of a second embodiment of a satellite pacing unit.
Figure 9:
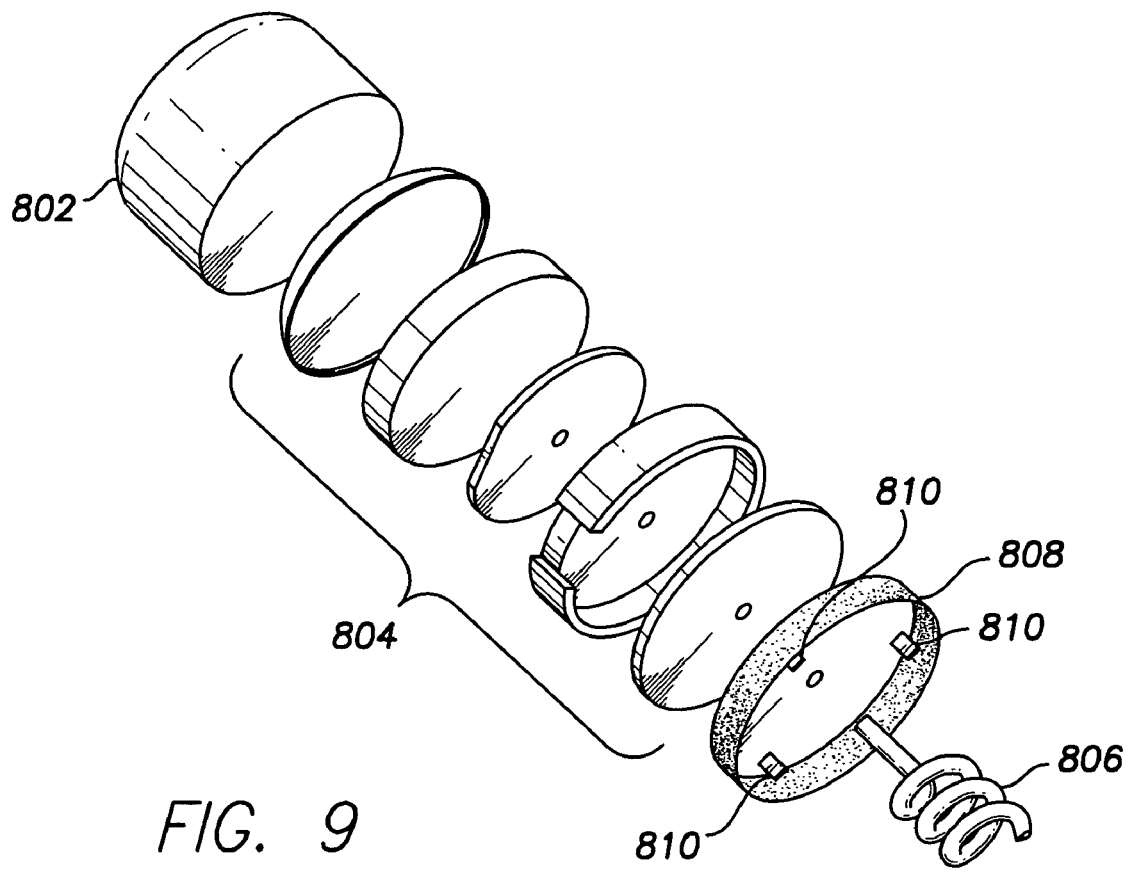
FIG. 9 is an exploded perspective view of the satellite pacing unit shown in FIG. 8.

FIGS. 8–9 show a second embodiment of satellite pacing unit 106. This embodiment comprises a casing 802 containing the several operating elements, generally designated 804, of the pacing unit. A base portion 808 is mounted to one end of casing 802 to seal operating elements 804 (e.g., circuit board, spacer and battery) within casing 802. Similar to the embodiment of FIGS. 6–7, an elongated member 806 extends out of base portion 808. Advantageously, member 806 has a helical or screw-like shape. This permits member 806 to be "screwed" into the epicardium of the heart. In a similar manner as elongated member 606, member 806 made be made to elute a steroid to reduce irritation and promote healing of an affected tissue region when member 806 is inserted into the heart. Gel-like material 608 may also be incorporated into this embodiment.

One of the problems encountered with satellite pacing units that are affixed to the heart by a screw member is the irritation of the heart tissue that occurs due to movement of the screw member as the heart beats. This irritation causes the body to build up scar tissue around the invasion area of the screw member. As scar tissue builds up, more voltage is needed to shock the heart and perform the necessary pacing functions. This results in shorter battery life and a requirement for more frequent replacements. For example, whereas the normal life of the satellite pacing unit is about two years, due to the scar tissue buildup around the screw, battery life may be shortened to only about six months. More frequent replacement of the satellite pacing unit requires more frequent invasive surgeries, with their attendant risks.

To alleviate this problem, a plurality of short protrusions, or "dirks", 810 are formed or mounted on the exterior face of base portion 804. In one example, dirks 810 are formed integrally with base 804. When pacing unit 106 is mounted to the heart wall, dirks 810 extend into contact with the pericardium (or, if the pericardium has been removed, as in the case of bypass surgery, in contact with the epicardium) to anchor unit 106 to the heart. Dirks 810 absorb most of the X-Y stress of the heart movement (Z-axis stress being in the direction of the longitudinal axis of member 806) to minimize the transmission of this load to member 806 and thereby substantially prevent irritation of the heart tissue by stress movement of member 806. Preferably, dirks 810 are not coated with steroid eluting material. It is desired that dirks 810 irritate the heart tissue to promote fibrosis. This causes scar tissue to build up around dirks 810 and further secure pacing unit 106 to the heart.

In each of the examples shown in FIGS. 6–7 and FIGS. 8–9, base portions 604 and 808, respectively, may be made of titanium. Members 606 and 806 may be formed of a 90/10 platinum-iridium mixture or an 80/20 platinum-iridium mixture. Clearly other materials and/or mixtures having characteristics suitable for use in the environment of this invention could be used for any of members 604, 606, 806 and 808, as would be apparent to one skilled in the relevant arts.

CONCLUSION

The foregoing discussion describes a cardiac system having a master pacing unit and at least one satellite pacing unit. The combined system provides full function pacing, while foregoing the difficulty of passing a left-side lead into the coronary sinus vein. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac system comprising:
   a master pacing unit operative to generate pacing pulses to be delivered to a portion of a patient's heart;
   at least one lead connected to the master pacing unit and configured for placement in electrical communication with a heart chamber; and
   a satellite pacing unit remote from the master pacing unit and operative to apply pacing pulses to a different portion of the patient's heart, said satellite pacing unit comprising:
   a housing having a base portion;
   an elongated member extending outwardly from said base portion for insertion into the patient's heart tissue, wherein the elongated member comprises an electrode for carrying electrical current from the pacing unit to the patient's heart; and
   a gel-like material affixed to said base portion for placement into contact with the patient's heart tissue, wherein said gel-like material is composed of an electrically conductive material to provide a complete electrical path for current generated from said elongated member.

2. An implantable cardiac system as recited in claim 1, wherein the elongated member has a substantially helical shape to enable the elongated member to be screwed directly into the epicardium of the patient's heart.

3. An implantable cardiac system as recited in claim 2, wherein the elongated member contains a steroid eluding material thereon.

4. An implantable cardiac system as recited in claim 1, wherein the said gel-like material contains a steroid.

5. An implantable cardiac system as recited in claim 4, wherein said steroid comprises dexamethazone sodium phosphate.

6. An implantable cardiac system as recited in claim 1, wherein said gel-like material comprises polyvinlpyrrolidone.

7. An implantable cardiac system as recited in claim 1, wherein, when implanted into a patient's body, the master pacing unit is electrically coupled to the right side of the patient's heart via one or more leads that position one or more electrodes in the right ventricle and one or more electrodes in the right atrium.

8. An implantable cardiac system as recited in claim 7, wherein, when implanted into a patient's body, the satellite pacing unit is affixed to the left side of the patient's heart in electrical contact with the left ventricle.

9. An implantable cardiac system as recited in claim 8, wherein the satellite pacing unit applies the pacing pulses in response to a signal wirelessly transmitted from the master pacing unit.

10. An implantable cardiac system as recited in claim 1, further comprising:
   a first communications module coupled to said master pacing unit to transmit a pacing command; and
   a second communications module coupled to said satellite pacing unit to receive the pacing command from the master pacing unit; wherein the first and second communication modules employ high frequency modulation to facilitate wireless communication between the master pacing unit and the satellite pacing unit.

11. An implantable cardiac system as recited in claim 10, wherein the satellite pacing unit is configured to apply the pacing pulses to the left side of the patient's heart in response to the pacing command wirelessly received from the master pacing unit.

12. An implantable cardiac system as recited in claim 10, wherein the satellite pacing unit is further equipped with sensing circuitry to sense cardiac activity, the satellite pacing unit being configured to apply the pacing pulses to the left side of the patient's heart in response to sensed cardiac activity.

13. An implantable cardiac system as recited in claim 10, wherein the satellite pacing unit is further equipped with sensing circuitry to sense cardiac activity, the satellite pacing unit being configured to apply the pacing pulses to the left side of the patient's heart in response to sensed cardiac activity in combination with receipt of the pacing command from the master pacing unit.

14. An implantable cardiac system as recited in claim 10, wherein the satellite pacing unit is further equipped with sensing circuitry to sense cardiac activity, the satellite pacing unit being configured to collect data pertaining to the cardiac activity and to transmit the data wirelessly to the master pacing unit.

15. A cardiac pacing unit implantable into a patient for attachment to the patient's heart, comprising:
 a housing having a base portion;
 an elongated member extending outwardly from said base portion for insertion into the patient's heart tissue, wherein the elongated member comprises an electrode for carrying electrical current from the pacing unit to the patient's heart; and
 a gel-like material affixed to said base portion for placement into contact with the patient's heart tissue to facilitate adherence of said satellite pacing unit to the patient's heart, wherein said gel-like material is composed of an electrically conductive material to provide a complete electrical path for current generated from said elongated member.

16. A cardiac pacing unit as recited in claim 15, wherein the elongated member has a substantially helical shape to enable the elongated member to be screwed directly into the epicardium of the patient's heart.

17. A cardiac pacing unit as recited in claim 16, wherein the elongated member contains a steroid eluding material thereon.

18. A cardiac pacing unit as recited in claim 15, wherein the elongated member contains a steroid eluting material thereon.

19. A cardiac pacing unit as recited in claim 15, wherein the said gel-like material contains a steroid.

20. A cardiac pacing unit as recited in claim 19, wherein said steroid comprises dexamethazone sodium phosphate.

21. A cardiac pacing unit as recited in claim 15, wherein said gel-like material comprises polyvinlpyrrolidone.

22. An implantable cardiac system comprising:
 a master pacing unit electrically coupled to deliver pulses to a right side of a patient's heart via one or more leads; and
 a leadless satellite pacing unit coupled to deliver pulses to a left side of the patient's heart under control of the master pacing unit, said leadless satellite pacing unit comprising:
 a housing having a base portion;
 an elongated member extending outwardly from said base portion for insertion into the patient's heart tissue, wherein the elongated member comprises an electrode for carrying electrical current from the pacing unit to the patient's heart; and
 a gel-like material affixed to said base portion for placement into contact with the patient's heart tissue, wherein said gel-like material is composed of an electrically conductive material to provide a complete electrical path for current generated from said elongated member.

23. An implantable cardiac device as recited in claim 22, wherein the master pacing unit communicates with the leadless satellite pacing unit via a wireless communication link.

24. An implantable cardiac device as recited in claim 22, wherein the leadless satellite pacing unit comprises sensing circuitry to sense cardiac activity, the satellite pacing unit being configured to deliver pulses in response to at least one of commands received from the master pacing unit or sensed cardiac activity.

25. A cardiac pacing unit as recited in claim 22, wherein the elongated member has a substantially helical shape to enable the elongated member to be screwed directly into the epicardium of the patient's heart.

26. A cardiac pacing unit as recited in claim 25, wherein the elongated member contains a steroid eluting material thereon.

27. A cardiac pacing unit as recited in claim 22, wherein the said gel-like material contains a steroid.

28. A cardiac pacing unit as recited in claim 27, wherein said steroid comprises dexamethazone sodium phosphate.

29. A cardiac pacing unit as recited in claim 28, wherein said gel-like material comprises polyvinlpyrrolidone.

* * * * *